United States Patent [19]
Wattanasirichaigoon

[11] Patent Number: 5,769,848
[45] Date of Patent: Jun. 23, 1998

[54] ENDOSCOPIC INSTRUMENT

[76] Inventor: Somkiat Wattanasirichaigoon, 197 Kent St. Apartment No. 47, Brookline, Mass. 02146

[21] Appl. No.: 645,520

[22] Filed: May 14, 1996

[51] Int. Cl.$^6$ ................................................ A61B 17/36
[52] U.S. Cl. .............................. 606/46; 606/41; 606/215; 606/219
[58] Field of Search ........................ 606/38–52, 213–221

[56] References Cited

U.S. PATENT DOCUMENTS

| | | |
|---|---|---|
| 1,741,461 | 12/1929 | Herman . |
| 2,004,559 | 6/1935 | Wappler et al. . |
| 3,882,854 | 5/1975 | Hulka et al. ................................. 128/6 |
| 4,233,493 | 11/1980 | Nath ........................................ 219/354 |
| 4,811,733 | 3/1989 | Borsanyi et al. . |
| 4,953,559 | 9/1990 | Salerno ................................... 128/751 |
| 5,015,249 | 5/1991 | Nakao et al. . |
| 5,201,740 | 4/1993 | nakao et al. ............................ 606/113 |
| 5,207,691 | 5/1993 | Nardella .................................. 606/142 |
| 5,217,458 | 6/1993 | Parins . |
| 5,261,918 | 11/1993 | Phillips ..................................... 606/41 |
| 5,295,900 | 3/1994 | Levin . |
| 5,304,183 | 4/1994 | Gourlay et al. ......................... 606/142 |
| 5,306,280 | 4/1994 | Bregen et al. . |
| 5,330,486 | 7/1994 | Wilk . |
| 5,336,229 | 8/1994 | Noda ....................................... 606/144 |
| 5,389,098 | 2/1995 | Tsuruta et al. ............................ 606/41 |
| 5,397,320 | 3/1995 | Essig et al. . |
| 5,403,312 | 4/1995 | Yates et al. . |
| 5,456,684 | 10/1995 | Schmidt et al. . |
| 5,669,934 | 9/1997 | Sawyer ................................... 606/213 |

OTHER PUBLICATIONS

Curet, M.J., et al.,Laparascopic Antegrade Sphincterotomy, *Annals of Surgery*, 221(2):149–155 91995).

Greenberger, N.J. and Isselbacher, K.J, "Diseases of the Gallbladder and Bile Ducts" in *Harrison's Principles of Internal Medicine*, Twelfth Edition eds. (NY: McGraw–Hill, Inc.), pp. 1358–1368 (1991).

*Primary Examiner*—David M. Shay
*Attorney, Agent, or Firm*—Hamilton, Brook, Smith & Reynolds, P.C.

[57] ABSTRACT

An endoscopic instrument comprising an elongate body having a proximal end and a distal end. Actuating mechanism is located at the proximal end and operating mechanism at the distal end. The operating mechanism comprises a pair of V-shaped jaw members, a cautery wire associated with jaw members to incise tissue gripped by the jaws and a mucosa-protecting balloon attached to and movable with one of the jaw members.

24 Claims, 7 Drawing Sheets

ENDOSCOPIC INSTRUMENT

BACKGROUND OF THE INVENTION

This invention relates to endoscopic instruments in general and more particularly to instruments for laparoscopic-assisted antegrade sphincterotomy/ sphincteroplasty. Whereas the invention pertains to sphincterotomy and sphincteroplasty, it has utility in other endoscopic instruments, for example those employed in incising all of the hollow viscuses and making an anastomosis of the gall bladder, small intestine, bowel, pancreas, etc.

Bile formed in the liver is secreted into a complex network of ducts, eventually entering into the common hepatic duct. Bile concentrated in the gallbladder is secreted into the cystic duct, which joins the hepatic duct to form the common bile duct (CBD). The common bile duct, in turn, is joined by the pancreatic duct whereupon the common bile duct enters the duodenum. The duodenum is the first segment of the small intestine. A sphincter (annular muscle surrounding an orifice opens and closes the orifice) is present at the duct-duodenum juncture.

Principal components of bile are the bile acids, which are detergents that aid in the excretion of cholesterol and digestion of fatty foods. Increased excretion of cholesterol is a major contributing factor in the formation of gallstones (cholelithiasis). Gallstones are quite prevalent in most western countries. For example, in the United States, at least 20% of women, and 8% of men over the age of 40 are affected by gallstones. It is estimated that 16 to 20 million people in the U.S. have gallstones, and that approximately 1 million new cases of cholelithiasis develop every year. Passage of gallstones into the common bile duct (choledocholithiasis) occurs in approximately 10 to 15% of patients with gallstones, and this percentage increases with age. (HARRISON'S PRINCIPLES OF INTERNAL MEDICINE, Twelfth Edition, McGraw-Hill, Inc., New York N.Y., pp. 1358–1368 (1991)).

Gallstones usually produce noticeable symptoms by causing inflammation, narrowing (stenosis) or obstruction of the cystic duct, common bile duct or sphincter following their exit from the gallbladder. Although there has been some success with drug- or shockwave-mediated dissolution of gallstones, the current therapy of choice is surgical intervention, either by excision of the gallbladder (cholecystectomy) or clearing the gallbladder (cholecystostomy). (HARRISON'S PRINCIPLES OF INTERNAL MEDICINE, Twelfth Edition, McGraw-Hill, Inc., New York, N.Y., pp. 1358–1368 (1991)). Typically, the cholecystectomy is performed with the aid of a laparoscope (a long slender optical instrument for insertion into the abdomen to visualize the interior of the abdominal cavity) and requires only a few small surgical incisions in the abdominal wall. This minimally invasive surgical technique provides many benefits to the patient, for example, shorter postoperative recovery time, less pain and complications.

A common situation encountered in patients undergoing laparoscopic surgery for gallstones is the discovery of previously undetected stones within the common bile duct (choledocholithiasis). Commonly, these stones are unable to pass through the sphincter, and out of the body through the intestines. To permit the passage of the stones, either a sphincterotomy (incision of the sphincter) or a sphincteroplasty (e.g., making a permanent opening by suturing at each cut edge of the sphincter) is required.

This situation presents a difficult problem for the surgeon and the surgeon is faced with a number of options. Two of them are widely accepted. With the first option, the surgeon converts the endoscopic/laparoscopic surgical procedure to open laparotomy with conventional surgical incisions. However, current methods of stone retrieval are limited and those patients with multiple stones are subjected to prolonged surgery.

With the second option, the surgeon completes a laparoscopic cholecystectomy. He then schedules an endoscopic retrograde sphincterotomy and stone retrieval at a later date. However, this subjects the patient to a second surgical procedure accompanied by the risks associated with another surgery, increased cost and prolongs the recovery period. With both of these options, the initial benefits of minimally invasive surgical technique are substantially diminished.

Recent reports have indicated another option in which the surgeon attempts antegrade sphincterotomy ((Curet, M.J., et al., Annal. Surg., 221:149–155 (1995)). Antegrade sphincterotomy is a procedure which cuts the sphincter by inserting an instrument through the cystic duct, along the common bile duct to the sphincter (i.e., in the direction of the flow of the bile). Unfortunately, there is difficulty in using a side-viewing scope to visualize the ampulla and the site of sphincterotome due to patient's supine position and excessive distention of the small intestine.

Clear visualization of the common bile duct and sphincter is key to the success of this surgery. Major blood vessels are located alongside the common bile duct. Moreover, the common bile duct lies adjacent to the liver, pancreas and small intestine, and the sphincter itself forms the juncture between the duct and the duodenum.

Furthermore, with laparoscopic procedures, depth perception is a serious problem. The mucosa of the duodenum contains many villi, is pleated, in part bulbous and, hence, is extremely irregular in form and shape. With open surgery, specific tissue can be cut without damaging the background tissue because the surgeon has a clear view and easy access to the surgical field. However, depth information is difficult to determine using a laparoscope, and serious complications can arise if the surgical procedure is not performed correctly because of initial inflation of the abdominal area.

There clearly exists a need for techniques and surgical instruments adapted to perform antegrade sphincterotomy procedures with facility and security.

SUMMARY OF THE INVENTION

The invention resides in an endoscopic instrument comprising an elongated body having a proximal end and a distal end. Actuating mechanism is located at the proximal end and operating mechanism is located at the distal end. The operating mechanism comprises a first V-shaped jaw member pointing toward the proximal end of the instrument and a second V-shaped jaw member pivotally attached to the first jaw member at the open end of the V. A cautery wire is associated with the second jaw member and a mucosa-protecting balloon is attached to and is movable with the second jaw member. The cautery wire is heatable in order to cauterize the incision which it makes.

A working channel or sheath into which the distal end of the instrument may be inserted is employed to insert the instrument into a patient.

In one embodiment of the invention, one of the jaw members is fixed to the body of the instrument and the other is pivoted on the fixed jaw member. In another embodiment of the invention, the jaw members constitute a clip which is separable from the instrument. Forceps are located at the distal end of the instrument for positioning the clip in an operative field. The clip is dissolvable in the patient and may be made of e.g., a dissolvable material such as polyglycolic acid.

One of the jaw members of the clip is provided with small wire-like spikes to grasp tissue in order that it may remain in place after the instrument has been withdrawn from a patient or until the clip dissolves in the patient. The cautery wire is removable from the clip after it has been pivoted into the tissue grasping position.

The above and other features of the invention including various and novel details of construction and combination of parts will now be more particularly described with reference to the accompanying drawings and pointed out in the claims. It will be understood that the particular device for laparoscopic assisted antegrade sphincterotomy/sphincteroplasty embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 11:
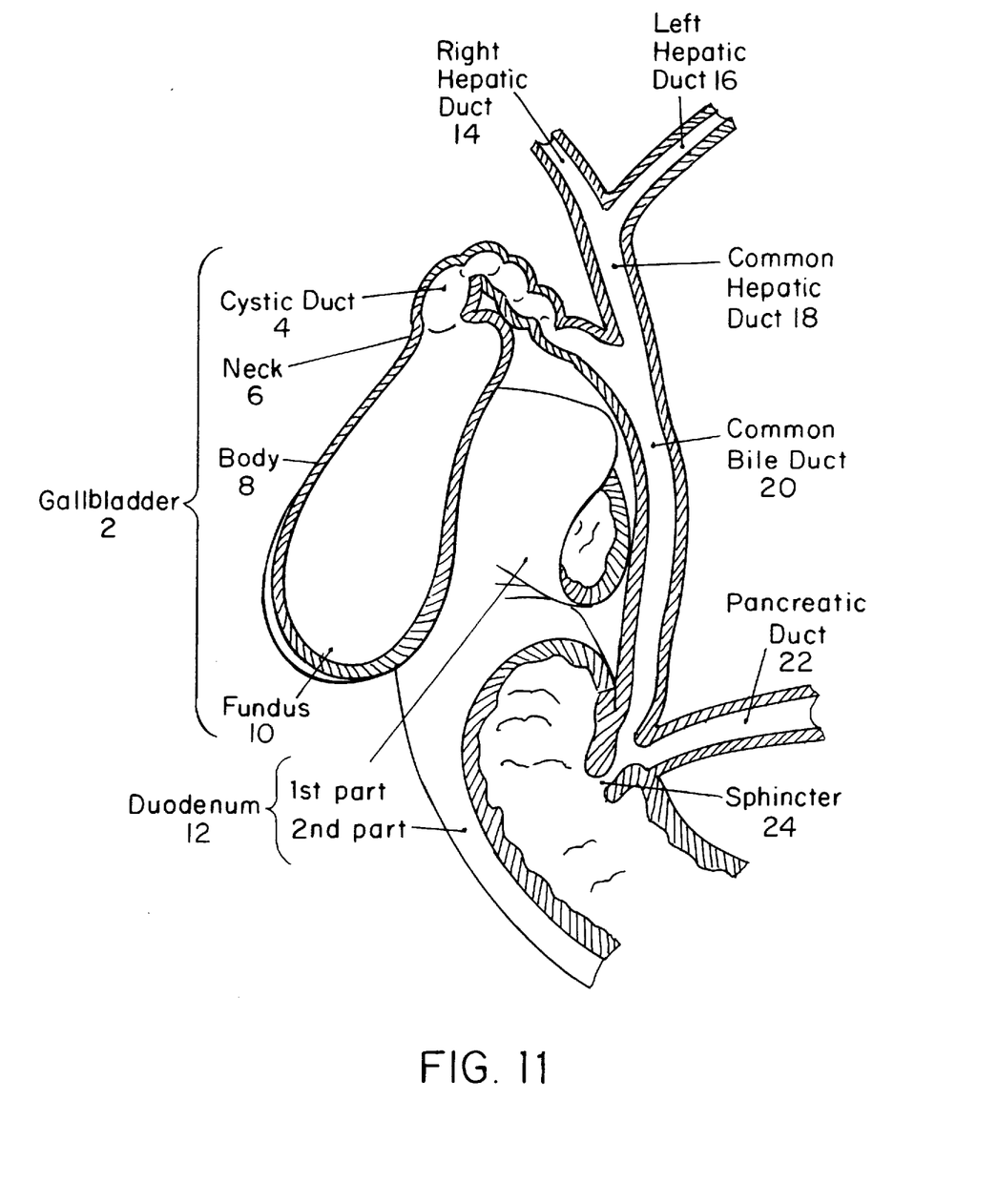
FIG. 11 is a schematic view of the duct-duodenum juncture.

FIG. 11 includes the gallbladder, generally indicated 2, the cystic duct 4, neck 6, gallbladder body 8 and the fundus 10. Also included is the duodenum 12 and the various ducts leading to and from these organs. Included are the right and left hepatic ducts 14 and 16, respectively, the common hepatic duct 18, the common bile duct 20, the pancreatic duct 22. At the junction of the common bile duct and the pancreatic duct is the sphincter 24 where gallstones collect and where instruments embodying the features of this invention will be used.

Figure 1:
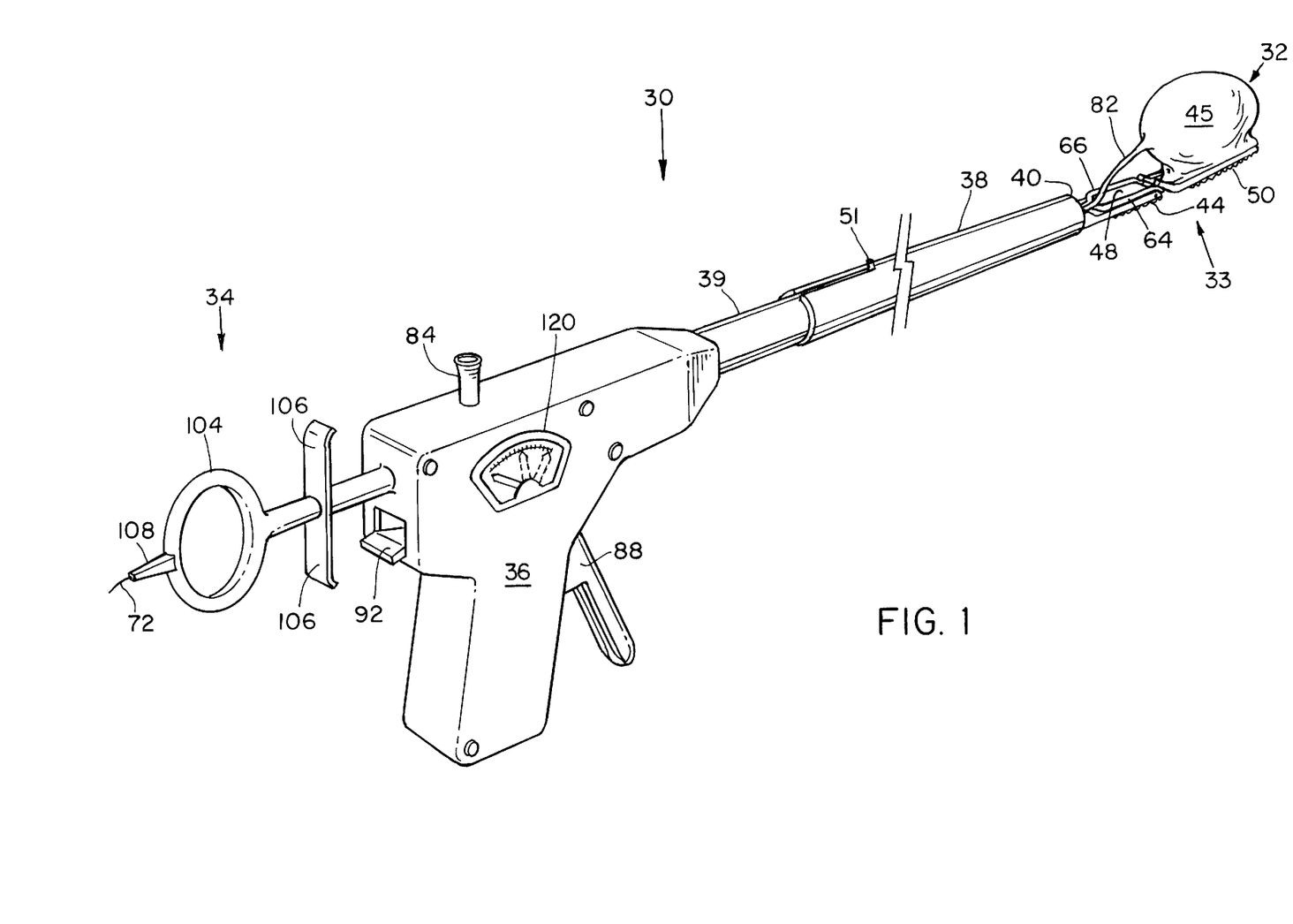
FIG. 1 perspective view of an antegrade sphincterotome embodying features of the present invention.

FIG. 1 is a perspective view of an antegrade sphincterotomy (instrument for incising a sphincter) generally designated 30. It has a distal end 32 where the actual operating elements 33 are located and a proximal end 34 where the activating elements are located including a pistol grip 36 for controlling the operating instruments which will be described in greater detail hereinafter. A generally, flexible, elongate tubular body 39 or body tube as it may also be called, extends from the pistol grip 36. The operating instruments project from the distal end 40 of the tube 39.

Figure 3:
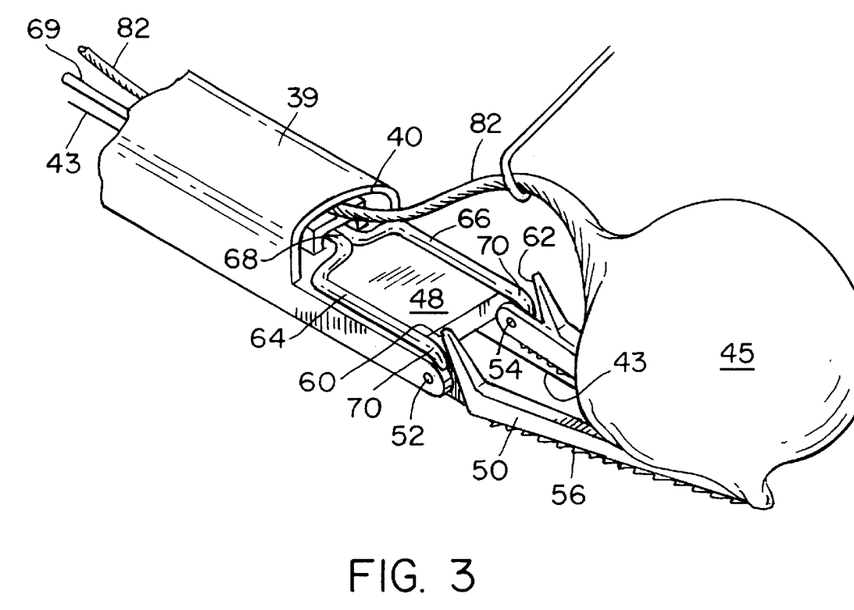
FIGS. 3 and 4 are detail perspective views of the functional portions of the sphincterotome shown in progressive stages.
Figure 4:
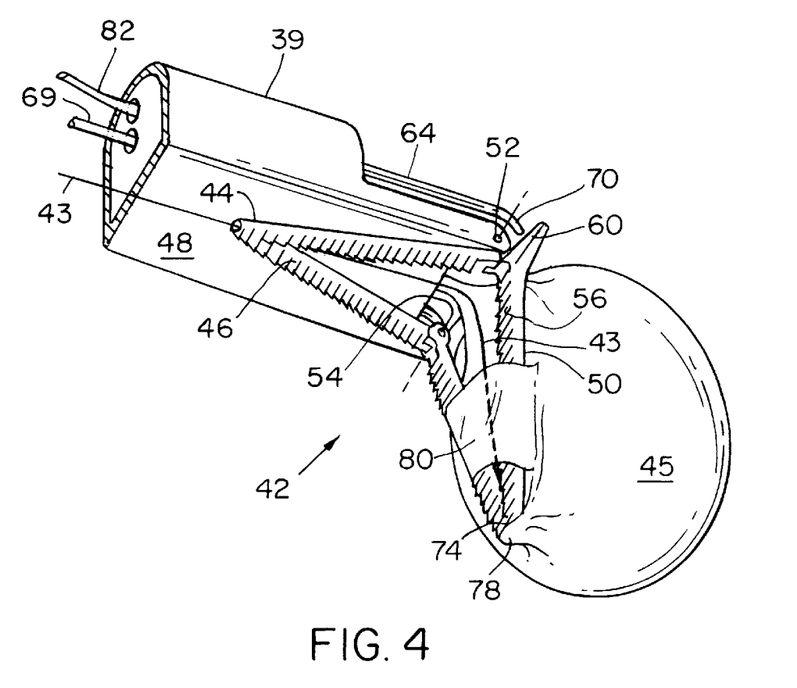

Referring next to FIGS. 3 and 4, the sphincterotomy instrument per se comprises a pair of articulated clamping jaws generally indicated 42, a stainless steel cautery wire 43 and an inflatable balloon 45, made of neoprene or any other bio-compatible material. It includes a first, generally open ended, V-shaped fixed jaw member 44 also called the proximal view. It includes serrations 46 on its bottom or exposed side as viewed in FIG. 4. Its upper side is fixed to a plate 48 extending from the distal end 40 of the body tube 39.

A second, pivotal jaw member 50 also called the distal jaw, which is essentially the mirror image of the jaw member 44, is pivotally hinged at 52 and 54 to the first or upper jaw member 44. The jaw member 50 also includes serrations 56. A pair of fingers 60 and 62 are formed on the second or movable jaw member 50 close to the pivots 52, 54.

A pair of push rods 64, 66 extend from the distal end 40 of the body tube 39. The rods are joined at 68 and extend from a rod 69. Each rod 64, 66 has a downwardly extending curved portion 70 which are engagable with the upwardly inclined fingers 60, 62. The cautery wire 43 extends from the apex 74 of the lower or movable jaw member 50.

The inflatable balloon 45 is attached to the apex 74 of the movable jaw member 50 at 78 and is held in place by a band or loop 80 through which the movable jaw member 50 extends. The band may also be secured to the nonserrated side of the jaw 50. The cautery wire 43 passes between the band 80 and the balloon 45. The balloon 45 has an integral tube 82 extending into the body tube 39 and re-emerging in the form of a filler valve 84 seen in FIGS. 1 and 2 at the top of the pistol grip 36.

Figure 2:
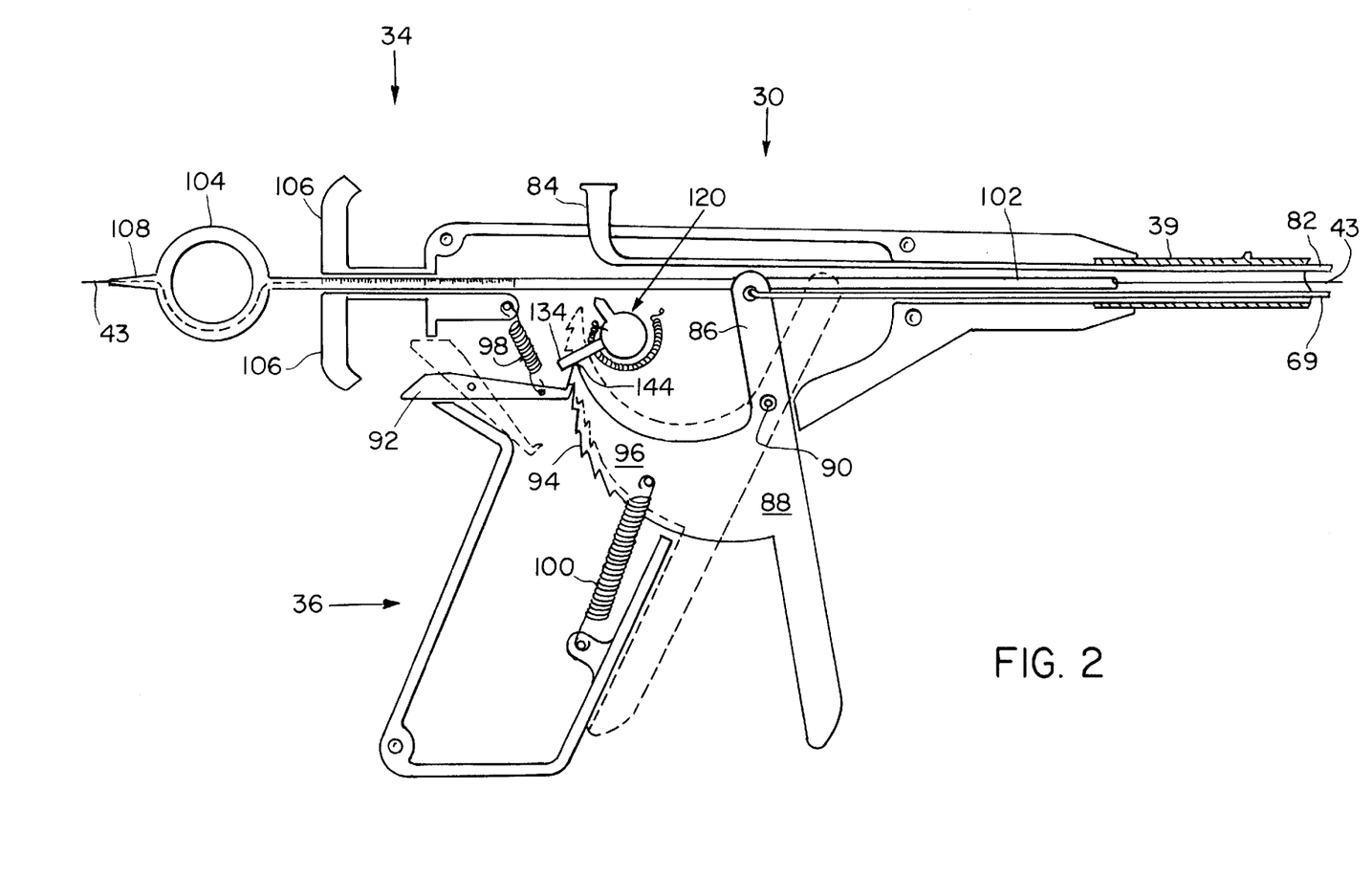
FIG. 2 side view of the proximal portion of the instrument shown in FIG. 1 with parts broken away for clarity.

FIG. 2 shows the proximal portion 34 of the sphincterotomy instrument including controlling mechanism grip 36. Push rod 69 will be seen extending rearwardly through the body tube 39. The rod is connected to the upper arm 86 of an actuating lever 88 pivoted in the pistol grip 36 at 90. The lever 88 is held in the FIG. 2 position by a pawl 92 which engages a tooth of a ratchet 94 on an arcuate portion 96 of the lever 88. The pawl is held in engagement with a tooth by a spring 98 assisted by a spring 100 which tends to urge the lever 88 in a counterclockwise position about the pivot 90. Upon moving the pawl 92 from the solid to the dotted line position permits the surgeon to squeeze the lever 88 and actuate the push rod 69. Movement of the lever 88 or trigger, as it can also be called, in a clockwise direction about the pivot 90 causes the push rod 69 to move to the right as viewed in FIG. 2.

The cautery wire 43 is attached to an insulated wire 102 which passes through the pistol grip 36. The wire 102 is attached to a finger loop 104 surrounded by a pair of finger guides 106 secured to the pistol grip 31. A continuation of the cautery wire 43 extends from a projection 108 on the ring 104 which permits it to be connected to a source of electric current to be heated.

Figure 5:
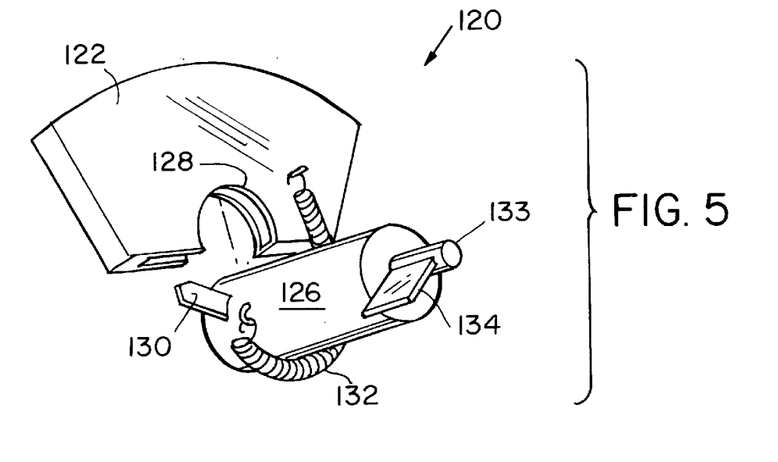
FIG. 5 is an exploded perspective view of a dial employed with the sphincterotome indicating degree of angular opening of the functional portion.
Figure 6:
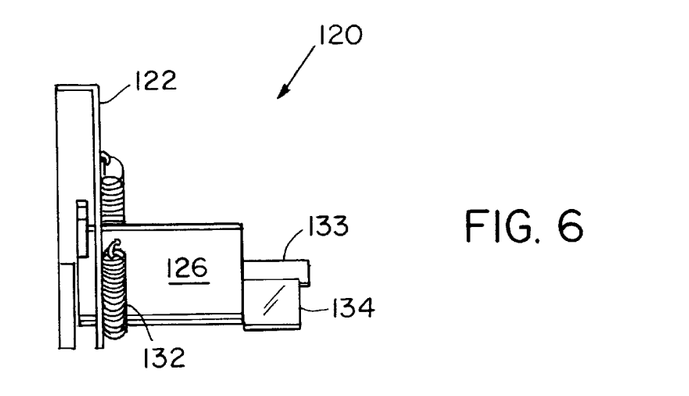
FIG. 6 is a side view thereof.
Figure 7:
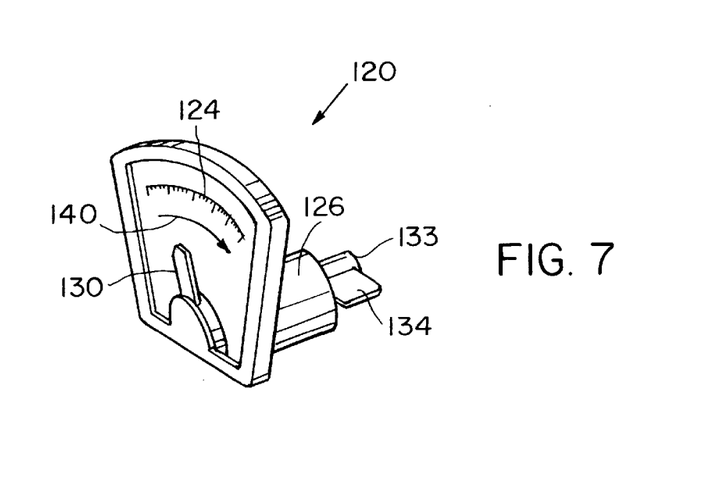
FIG. 7 is a reverse perspective view thereof.

A display dial 120 is located on the side of the pistol grip 36 and will be seen in detail in FIGS. 5–7. The dial indicates the amount of rotational movement of the movable jaw 50 relative to the stationary jaw 44. A dial indicator 122, made of clear plastic, has an arcuate scale 124 printed or otherwise marked on the plastic. A cylinder 126 is received within a partially circular cutout 128 in the indicator 122. A pointer 130 is fixed to the cylinder and is aimed at the scale 124. The cylinder is biased in a counterclockwise direction as seen in FIG. 5 by a tension spring 132. A pin 133, mounting a plate 134, extends from the cylinder 126 to impart rotary motion to the pointer 130 in the direction of the arrow 140 in FIG. 7.

As will be seen in FIG. 2, the arcuate portion 96 of the trigger or lever 88 has a tip 144 which is engagable with the plate 134 and when the surgeon squeezes the lever 88 to force the push rod forward to rotate the jaw 50, the cylinder 126 is urged in a clockwise direction against the force of the tension spring 132. The pointer 130 thus rotates relative to the dial 124 indicating the relative angle of degree between the fixed and rotary jaws.

One of the problems encountered in laparoscopic practice is the inability of the surgeon to have an accurate perception of depth and in the present instance due to the irregular mucosa. This is contrary to open surgery where the actual tissue or organ is exposed for direct view by the surgeon and, contrary to laparoscopic surgery, where the surgical field is viewed on a scope. While it is true that the laparoscopic camera can focus on the operative field, depth perception suffers. It is this aspect of the surgery that the mucosa-protecting balloon comes into play.

A working channel or the sheath 38 of the instrument itself is initially introduced into the patient over a conventional guide wire. It is advanced through an incision in the cystic duct along the common bile duct 4 toward the sphincter 24. Under laparoscopy, the surgeon can see the tip 74 of the instrument underneath the duodenal wall. The mucosa-protecting balloon 45 is collapsed and the jaws 44 and 50 in their open position, in other words, co-planar. Only the proximal jaw 44 is within the sheath 38. Next, the mucosa-protecting balloon is inflated through the valve 84 and the conduit 82. With the upward traction of the instrument, the sphincter is ready to access. Upon reaching the sphincter, the surgeon draws the sheath 38 toward the proximal end until the pin 51 (FIG. 1) on the tube 39 engages the end of the slot 53. The parts then assume the FIG. 1 configuration. With the mucosa-protecting balloon then inflated, the surgeon manipulates the sphincterotome until the jaws are arranged in the desired position relative to the sphincter muscle. Generally speaking, the proximal jaw 44 would be located at the inner portion of the sphincter muscle to be incised with the distal jaw 50 grasping upon the duodenal mucosa.

Since the duodenum mucosa contains villi and is of irregular shape, it could readily be injured by the distal jaw 50 and/or the cautery wire 43. During the operation, the balloon 45 functions as a buffer to move the mucous membrane or mucosa out of the operative field so that it does not become inadvertently damaged and to improve the view or depth perception of the operative field.

With the fixed or proximal jaw 44 in engagement with the inner portion of the sphincter which is to be incised, the cautery wire 43 is heated and the movable or distal jaw 50 moved from the FIG. 3 position gradually toward and then beyond the FIG. 4 position. The movable jaw 50 clamps the tissue against the fixed jaw 44. During this process, the balloon has been pressing or sliding against the surrounding mucosa and preventing the cautery wire from causing damage to the duodenal mucosa. After the tissue has been clamped and the cautery wire heated, the surgeon pulls on the loop 102 thus straightening the cautery wire 43 which has previously been looped around the tissue, thus simultaneously cutting and cauterizing the sphincter tissue.

Upon the completion of the procedure, the surgeon returns the jaws to the FIG. 3 or co-planar position, deflates the balloon 45 and withdraws the jaws and balloon into the sheath 38. The surgeon then withdraws the instrument from the common bile duct and from the patient.

At this time, stones which were blocked by the sphincter are free to pass from the sphincter into the second part of the duodenum 12 (see FIG. 12) and ultimately out through the intestine. If, in fact, the stones did not themselves pass through the incised sphincter 24, they may be extracted by the surgeon using another adjunctive instrument which may be inserted through the cystic duct and the common bile duct.

Another embodiment of the invention will now be described with reference to FIGS. 8, 9 and 10.

Figure 8:
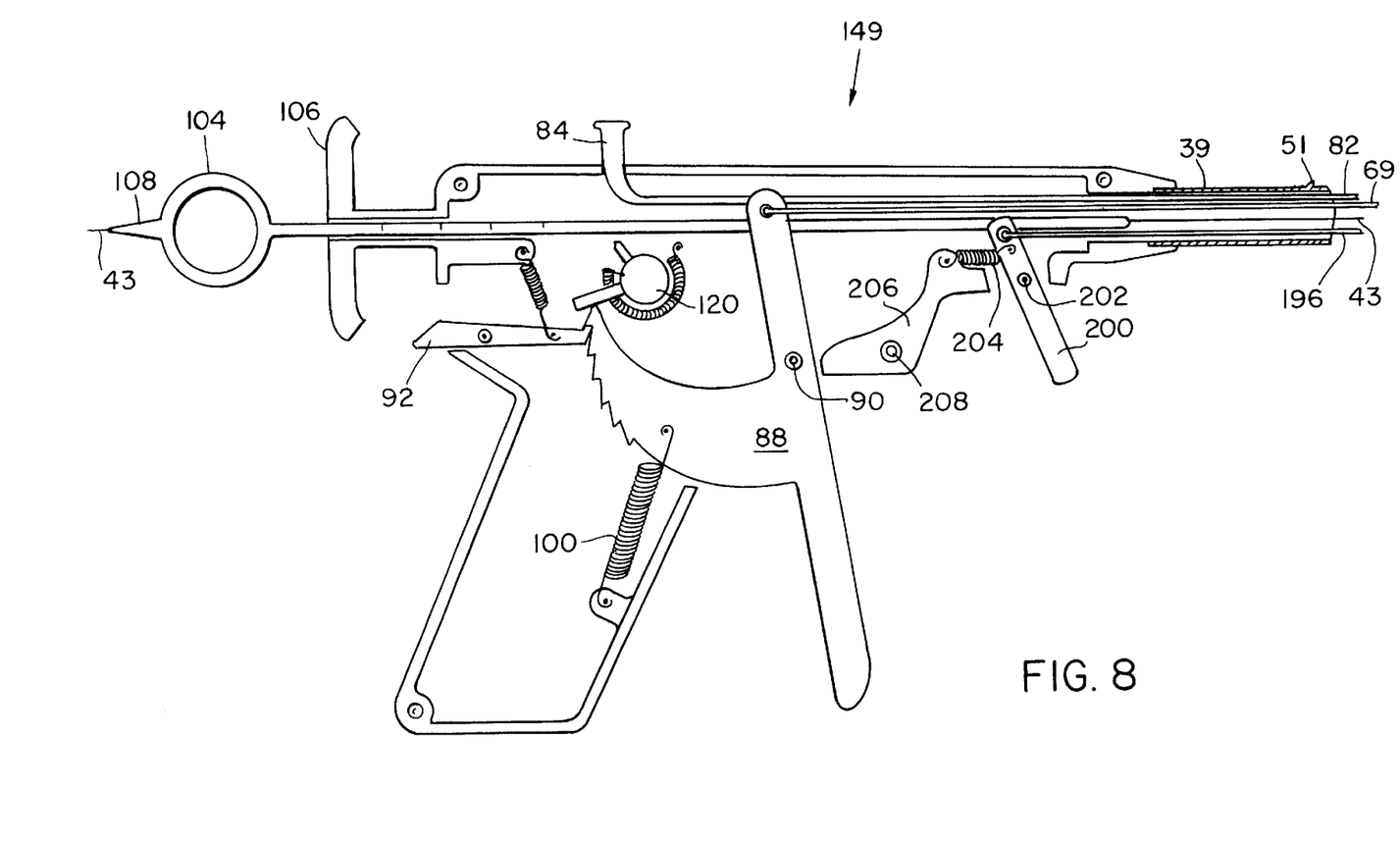
FIG. 8 is a side view, with parts removed for clarity, of a sphincteroplast instrument embodying the features of the present invention.
Figures 9, 10:
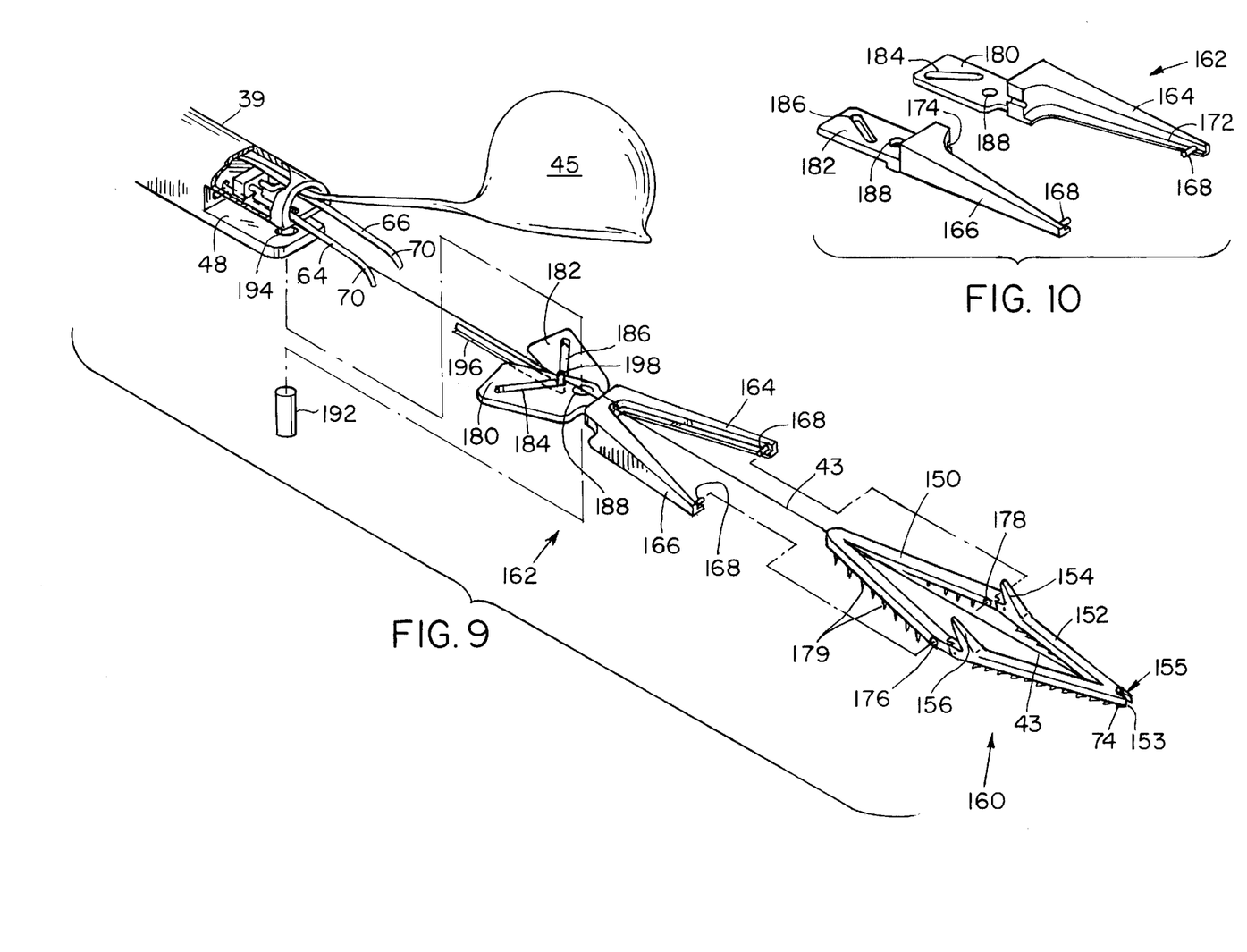
FIG. 9 is an exploded perspective view of the functional elements of the sphincteroplasty
FIG. 10 is an exploded perspective view of the arms of the clip applying element shown in FIG. 9.

Referring first to FIG. 9, a pair of hinged, V-shaped jaws, designated 150 and 152, are constructed similar to the jaws of the embodiment shown in FIGS. 1–4. However, in the embodiment shown in FIG. 8–10, the distal jaw 150 and the proximal jaw 152 are both made of relatively rigid but absorbable material. Polyglycolic acid has been found to be satisfactory. Proximal jaw 150, while similar to proximal jaw member 44 in the first embodiment, is not attached to the surface 48. Both jaws 150, 152, collectively referred to as clip 160, are free-floating and are separate from the instrument 149 per se. The proximal jaw 150 has small wire-like spikes 179 projecting from its lower surface (see FIG. 9) rather than being serrated like proximal jaw 44 of the first embodiment. Distal jaw 152 is, however, serrated. The clip 160 comprising the jaws 150, 152 is insertable in the patient and remain there for a period of approximately two weeks until it dissolves. As with the first embodiment, the sphincteroplasty instrument includes a mucosa-protecting balloon 45.

The clip is positioned by a forceps-like member, generally designated 162, having cooperative, movable blades 164 and 166. Each of the blades has a pin 168 at its distal end. The blades are provided with grooves 172, 174 (FIG. 10) along their inner edges. The width of the grooves are just slightly larger than the thickness of the jaw member 150 so that it may be gripped within the forceps-like blades with the pins entering holes 176 in the jaw member 150.

The blades 164, 166 each include a plate 180, 182 having a diagonal slot 184, 186. Each plate has a bore or circular opening 188. The plates are assembled as shown in the middle portion of the exploded view of FIG. 9 on a pin 192 which passes through a bore 194 in the plate 48. A push-pull rod 196 mounts an upstanding pin 198 at its distal end which is received within the assembled grooves 184, 186 in the plates 180, 182. The jaw 152 of the clip 160 is pivoted by fingers 70, 72 on push rods 64, 66 acting on the fingers in the same manner 154, 156 as with the FIG. 1 embodiment. A cautery wire 43 is removably attached at the apex 74 of the jaw member 152. It passes under the jaw 152, up and into a slot 153 in the apex of the jaw. it is knotted or has a bulge at its terminal end to retain it in the slot.

Movement of the rod 196 to the right, as viewed in FIG. 9, opens the forceps 162 whereupon a clip 160 may be inserted into the grooves 172, 174 of the forceps 162. Movement of the rod 196 to the left closes the forceps 162 upon the clip 160.

Referring next to FIG. 8, the push-pull rod 196 is attached to a lever 200, pivotally mounted at 202 to the sphincteroplasty instrument 149 which otherwise is similar to the sphincterotomy instrument 30 of the first embodiment. The lever 200 is urged in a counter-clockwise direction by a spring 204 secured to a bracket 206 pivotally mounted at 208 on the sphincteroplasty instrument 149.

In operation, the embodiment of FIGS. 8–10 functions much the same as the embodiment of FIG. 1. After the gallbladder has been removed, or while it is being removed, a dissolvable clip 160 is loaded into the forceps 162. The mucosa-protecting balloon 45 is attached to the distal end 74 of the clip and the sphincteroplasty instrument is inserted through the sheath 38 or its equivalent into the patient. Under laparoscopy, the surgeon can see the protrusion of the tip 74 of the clip 160 underneath the duodenal wall. The balloon 45 is inflated and the clip is oriented relative to the sphincter as are the jaws 44, 50 of the FIG. 1 embodiment. The distal jaw member 152, with the balloon attached, is pivoted downwardly and rearwardly toward the jaw 150 of the clip 160 compressing the portion of the sphincter to be incised between them. The wire-like spikes 179 of the jaw member 150 impinge upon the tissue of the sphincter while the serrated jaw member 152 compresses the tissue. With the tissue of the sphincter thus grasped, the heated cautery wire 43 is pulled to incise the tissue and the band 80 of the balloon 45. As a result, the balloon is detached from the clip 60. Upon the completion of the incision, the cautery wire pulls out from the slot 155 leaving the clip in place with the tissue incised essentially midway between the legs of the now closed V-shaped clip.

The balloon 45 is deflated, the forceps 162 are opened slightly and the instrument is removed from the patient leaving the clip 160 in place.

With time, the tissue within the grasp of the clip becomes necrotic and passes into the duodenum. In about two weeks, the clip itself dissolves and also passes into the duodenum and, thence, from the patient. Unlike the FIG. 1 embodiment where the incision is linear, the patient's sphincter has a permanent V-shaped aperture as a result of the above-described sphincteroplasty procedure.

I claim:

1. An endoscopic instrument comprising:
   an elongate body having a proximal end and a distal end;
   actuating mechanism at the proximal end and operating mechanism at the distal end;
   the operating mechanism comprising:
      a pair of V-shaped jaw members,
      a first jaw member pointing toward the proximal end of the instrument,
      the second jaw member being pivotally attached to the first jaw member of the open end of the V,
      a cautery wire extending from the second jaw member to the actuating mechanism; and
      a mucosa-protecting balloon attached to and movable with the second jaw member.

2. An instrument in accordance with claim 1, wherein the jaws are serrated.

3. An instrument in accordance with claim 1, wherein the instrument includes means for inflating and deflating the mucosa-protecting balloon.

4. An instrument in accordance with claim 1, wherein the instrument includes means for heating the cautery wire.

5. An endoscopic instrument comprising:
   an elongate body having a proximal end and a distal end;
   actuating mechanism at the proximal end and operating mechanism at the distal end;
   the operating mechanism comprising:
      a pair of V-shaped jaw members,
      one jaw member being fixed to the body and the other being pivotal on the fixed jaw member,
      a cautery wire extending from the second jaw member to the actuating mechanism: and
      a mucosa-protecting balloon attached to and movable with the pivotal jaw.

6. An instrument in accordance with claim 5, wherein the jaws are serrated.

7. An instrument in accordance with claim 5, wherein the instrument includes means for inflating and deflating the mucosa-protecting balloon.

8. An instrument in accordance with claim 5, wherein the instrument includes means for heating the cautery wire.

9. An endoscopic instrument comprising:
   an elongate body having a proximal end and a distal end;
   actuating mechanism at the proximal end and operating mechanism at the distal end;
   the operating mechanism comprising:
      pair of V-shaped jaw members,
      one jaw member being fixed to the body and the other being pivotal on the fixed jaw member,
      a cautery wire extending from the second jaw member to the actuating mechanism,
      a mucosa-protecting balloon attached to and movable with the pivotal jaw; and
      a working channel for assisting in inserting the instrument in a patient and through which channel the distal end of the instrument may be inserted.

10. An instrument in accordance with claim 9, wherein the jaws are serrated.

11. An instrument in accordance with claim 4, wherein the instrument includes means for inflating and deflating the mucosa-protecting balloon.

12. An instrument in accordance with claim 9, wherein the instrument includes means for heating the cautery wire.

13. An endoscopic instrument comprising:
   an elongate body having a proximal end and a distal end;
   actuating mechanism at the proximal end and operating mechanism at the distal end;
   the operating mechanism comprising:
      a clip removable from the instrument, said clip comprising a pair of V-shaped jaw members,
      a first jaw member pointing toward the proximal end of the instrument,
      the second jaw member being pivotally attached to the first jaw member at the open end of the V,
      a cautery wire extending from the second jaw member of the clip to the operating mechanism; and
      a mucosa-protecting balloon attached to a movable with the second jaw.

14. An endoscopic instrument according to claim 13, wherein the clip is made of absorbable material.

15. An endoscopic instrument according to claim 13, wherein the cautery wire is releasably secured to the second jaw member.

16. An endoscopic instrument according to claim 13, wherein the instrument includes means for heating the cautery wire.

17. An endoscopic instrument comprising:
   an elongate body having a proximal end and a distal end;
   actuating mechanism at the proximal end and operating mechanism at the distal end;
   operating mechanism comprising:
      a clip removable from the instrument comprising a pair of V-shaped jaw members,
      a first jaw member pointing toward the proximal end of the instrument,
      the second jaw member being pivotally attached to the first jaw member at the open end of the V,
      a cautery wire extending from the second jaw member of the clip to the operating mechanism,
      a mucosa-protecting balloon attached to and movable with the second jaw member; and forceps at the distal end of the instrument for positioning the clip in an operative field.

18. An endoscopic instrument according to claim 17, wherein the clip is made of absorbable material.

19. An endoscopic instrument according to claim 17, wherein the cautery wire is releasably secured to the second jaw member.

20. An endoscopic instrument according to claim 17, wherein the instrument includes means for heating the cautery wire.

21. An endoscopic instrument comprising:

an elongate body having a proximal end and a distal end;

actuating mechanism at the proximal end and operating mechanism at the distal end;

the operating mechanism comprising:

a clip removable from the instrument comprising a pair of V-shaped jaw members, a first jaw member pointing toward the proximal end of the instrument, the second jaw member being pivotally attached to the first jaw member at the open end of the V, a cautery wire extending from the jaw member of the clip to the operating mechanism, a mucosa-protecting balloon attached to and movable with the second jaw member, forceps at the distal end of the instrument for positioning the clip in an operative field; and a working channel for assisting in inserting the instrument in a patient and through which channel the distal end of the instrument may be inserted.

22. An endoscopic instrument according to claim 21, wherein the clip is made of absorbable material.

23. An endoscopic instrument according to claim 21, wherein the cautery wire is releasably secured to the second jaw member.

24. An endoscopic instrument according to claim 21, wherein the instrument includes a means for heating the cautery wire.

* * * * *